United States Patent [19]

Bennett

[11] Patent Number: 4,574,173
[45] Date of Patent: Mar. 4, 1986

[54] DEVICE FOR RF WELDING AN IV TUBE TO A CATHETER LUMEN

[75] Inventor: Laurence M. Bennett, Sandy, Utah

[73] Assignee: Warner-Lambert Company, Morris Plains, N.J.

[21] Appl. No.: 607,329

[22] Filed: May 4, 1984

[51] Int. Cl.$^4$ .............................................. H05B 6/54
[52] U.S. Cl. ........................... 219/10.53; 219/10.57; 219/10.67; 219/10.81; 604/96; 604/280; 156/273.7; 156/380.2
[58] Field of Search ................ 219/10.53, 10.57, 9.5, 219/8.5, 10.41, 10.43, 10.81, 10.67; 604/96, 264, 280; 156/272.2, 273.3, 273.7, 274.4, 379.6, 380.2, 380.6; 279/41 R

[56] References Cited

U.S. PATENT DOCUMENTS

| | | |
|---|---|---|
| 399,985 | 3/1889 | Goodwillie . |
| 2,561,569 | 7/1951 | Flynn ....................... 18/13 |
| 2,775,068 | 12/1956 | McDuffee ............... 219/10.53 X |
| 2,876,358 | 3/1959 | Root ....................... 219/10.53 |
| 3,064,653 | 11/1962 | Coanda .................... 128/348 |
| 3,174,890 | 3/1965 | Goyke ..................... 156/272 |
| 3,293,402 | 12/1966 | Graham .................. 279/41 X |
| 3,322,590 | 5/1967 | Clark ....................... 156/273 |
| 3,469,579 | 9/1969 | Hubert .................... 128/214.4 |
| 3,625,793 | 12/1971 | Sheridan ................. 156/229 |
| 3,720,210 | 3/1973 | Diettrich ................ 128/214.4 |
| 3,817,389 | 6/1974 | Weichselbaum ....... 210/448 |
| 3,959,058 | 5/1976 | Rath et al. ............. 156/380.2 X |
| 3,976,529 | 8/1976 | Weichselbaum ....... 156/272 |
| 4,050,667 | 9/1977 | Kossett ................... 249/82 |
| 4,072,146 | 2/1978 | Howes .................... 128/2.05 D |
| 4,072,153 | 2/1978 | Swartz .................... 128/350 R |
| 4,133,544 | 1/1979 | Halvorsen ............... 279/41 R X |
| 4,210,479 | 7/1980 | Fabisiewicz ............ 156/273 |
| 4,214,593 | 7/1980 | Imbruce et al. ........ 128/748 |
| 4,248,224 | 2/1981 | Jones ...................... 128/214 R |
| 4,268,338 | 5/1981 | Peterson ................. 156/251 |
| 4,309,994 | 1/1982 | Grunwald ............... 128/214 R |
| 4,354,495 | 10/1982 | Bodicky .................. 128/348 |
| 4,364,394 | 12/1982 | Wilkinson ............... 604/96 |
| 4,384,186 | 5/1983 | Burt ........................ 219/10.81 |
| 4,398,910 | 8/1983 | Blake et al. ............ 604/93 |
| 4,405,313 | 9/1983 | Sisley et al. ............ 604/43 |
| 4,406,656 | 9/1983 | Hattler et al. .......... 604/280 |
| 4,419,095 | 12/1983 | Nebergall et al. ...... 604/96 |

Primary Examiner—Philip H. Leung
Attorney, Agent, or Firm—Neil K. Nydegger

[57] ABSTRACT

A device for welding an IV tube into fluid communication with a lumen of a catheter comprises a grounded metal adapter which is operatively associated with a dielectric collet to clampingly engage and hold a catheter in the collet. The device further comprises a metal mandrel which is partially inserted into an IV tube and positioned so that part of the IV tube and mandrel extend into a portion of a lumen of the catheter. With the IV tube and mandrel positioned in the lumen, the dielectric collet is further engaged to compressingly urge the lumen sidewall into contact with the outer surface of the IV tube. RF energy is then applied to the mandrel to weld the IV tube into the lumen.

18 Claims, 11 Drawing Figures

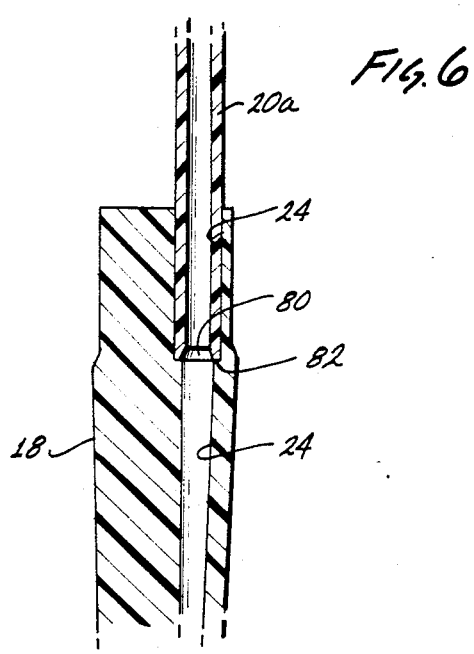
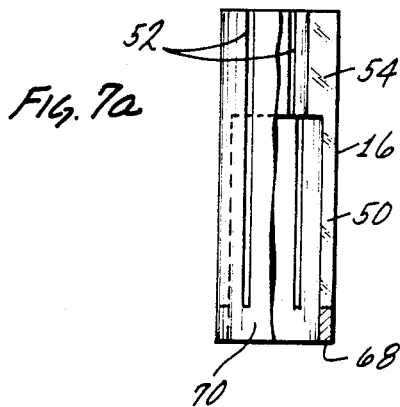
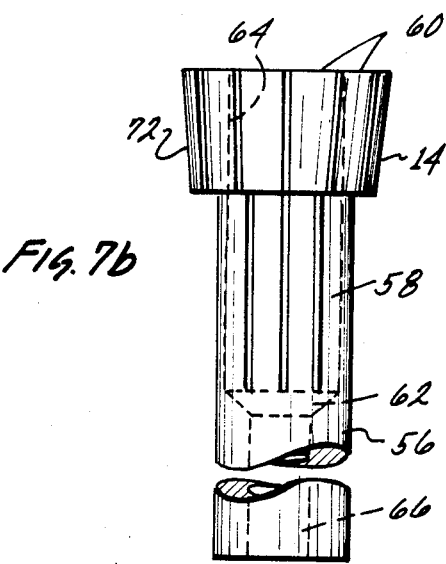
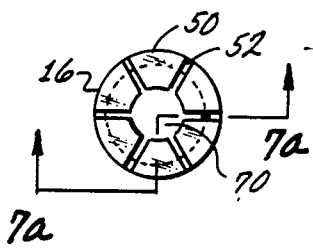
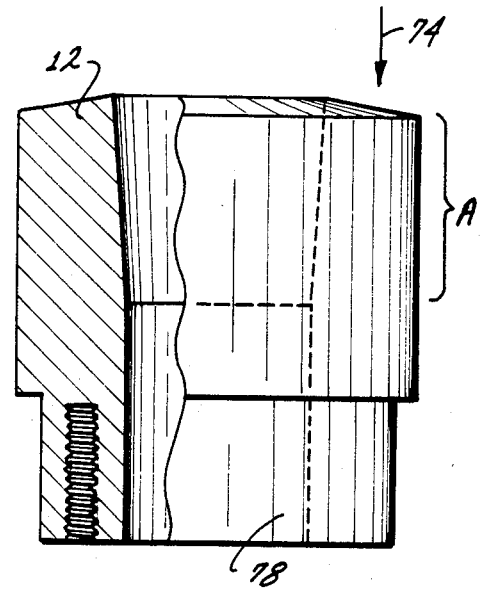
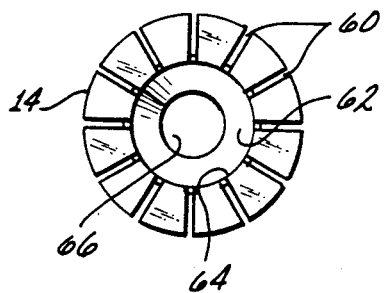

DEVICE FOR RF WELDING AN IV TUBE TO A CATHETER LUMEN

BACKGROUND OF THE INVENTION

The present invention relates generally to devices used for RF welding. More particularly, the present invention relates to a device for RF welding IV tubes into fluid communication with the lumens of a catheter. This invention is particularly, though not exclusively, useful for welding relatively thick-walled IV tubes of generally circular cross-section to lumens of generally noncircular cross-section.

DESCRIPTION OF THE PRIOR ART

Numerous health care situations are not uncommon wherein it is necessary to simultaneously give several different medications to the patient. In cases where the various medications can be given as solutions, it is often desirable to intravenously infuse them into the patient through a single puncture site with the use of a multilumen catheter. Indeed, the concept of using multilumen catheters for various medical purposes is well known in the pertinent art. For example, U.S. Pat. No. 4,405,313 to Sisley et al. discloses a dual lumen catheter suitable for surgical implantation. Other U.S. patents which include U.S. Pat. No. 550,238 to Allen, U.S. Pat. No. 3,394,705 to Abramson, U.S. Pat. No. 3,046,988 to Moreau et al., U.S. Pat. No. 3,448,739 to Stark et al., U.S. Pat. No. 3,746,003 to Blake et al., and U.S. Pat. No. 3,805,794 to Schlesinger each disclose multilumen or multi-passageway devices for use in the medical arts. Additionally, U.S. Pat. No. 4,072,146 to Howes and U.S. Pat. No. 4,406,656 to Hattler et al. disclose multilumen venous catheters which teach or suggest use of an adapter for connecting proximal IV tubes to the lumens of multilumen catheters.

Further, the use of an electronic welding current to join plastic parts is known in the art. Specifically, U.S. Pat. No. 3,322,590 to Clark discloses an electronic welding process for making a sealed connection between a tube and a container. Further, U.S. Pat. No. 4,210,479 to Fabisiewicz discloses a method for using RF energy to band a plastic tube to a metal needle and U.S. Pat. No. 4,268,338 discloses use of RF current to seal thermoplastic layers. In U.S. Pat. No. 4,419,095 to Nebergall et al. a method for RF welding a cannula with a radi-opague tip is disclosed wherein the inner and outer diameters of the mated elements are uniform so as to not produce projecting edges or ridges at the joint. In none of the cited references, however, is there any teaching of a connection or method for connecting proximal IV tubes with catheter lumens by RF welding to form a continuous and integral bond at the interface between the tube and the lumen.

A common problem with multilumen catheters is their size. In order to minimize trauma to the patient, it is desirable to have the smallest possible puncture. Consequently, a catheter should have the smallest possible cross-sectional area. At odds with this desire is the fact that the flow characteristics of medical solutions within a generally round lumen of a catheter improves with an increase in lumen cross-sectional area in accordance with Poiseuille's Law:

$$F = \frac{\Delta P \pi R^4}{8L}$$

where:
F=Flow
P=Pressure
R=Radius, and
L=Tube Length.

From Poiseuille's Law, it can be appreciated that flow characteristics vary proportionally with the square of the lumen's cross-sectional area. Thus, even moderate increases in lumen cross-sectional area can have a marked effect on flow characteristics. Accordingly, given a catheter having a generally circular cross-section, the shape of the individual lumens within the catheter is an important consideration for optimizing flow characteristics through the catheter.

It can be shown mathematically and empirically that lumens of circular cross-section do not optimize use of the available area in the cross section of a circular catheter. Instead, semi-circular or wedge shaped lumens appear to optimize such use. However, with semi-circular or wedge shaped lumens, the junctures between the surfaces that form the lumens create dead spaces and stagnation areas in the fluid flow. Eliptically shaped lumens, on the other hand, essentially eliminate flow problems caused by lumen wall junctures while at the same time using available catheter cross-section area more efficiently than circular-shaped lumens. Whereas a case can be made that eliptically shaped lumens are optimal for the design of a multilumen catheter, the preferred cross-section for an IV tube remains circular. Thus, for many applications it is necessary and desirable to join an IV tube of generally circular cross-section with catheter lumens which are generally of noncircular cross section.

Various methods for attaching IV tubes to catheters have been proposed in the prior art. For example, one method employs a thermoplastic adapter which is glued into place as a connector between the flared end of the catheter and the proximal IV tubes. Another presently used method requires the glueing of a metal tube into fluid communication between the catheter lumens and the lumen of the IV tube. The joint so formed is then encased in glue and surrounded by a thermoplastic sleeve. Still another method for attaching IV tubes to a catheter uses an insert molded connector for positioning and mating the fluid passageways of a catheter and an IV tube. In each of the above described methods, the connection requires at least one additional part and may even use dissimilar materials. Furthermore, these methods either require expensive injection molding equipment or use glue which can develop leaks and inconsistent pull strengths between the IV tube and the catheter.

Although RF welding, as previously noted, has been used in certain operations to weld plastic parts together, the RF welding of IV tubes to the lumens of a catheter poses several heretofore unsolved problems. First, it should be appreciated that RF welding is most effective where there is contact between the surfaces. Consequently, unless the lumen sidewall and the outer surface of the IV tube are placed into contact with each other, gaps and voids are created at the weld. To partially overcome this problem, thin walled IV tubes could be used with increased RF welding energy levels. The molten plastic tube created with this combination may tend to fill in the gaps and voids. Generally, however, thin walled IV tubes have certain disadvantages which make them less attractive for hospital use than the thicker walled tubes. For instance, thin walled tubes kink more easily than thicker walled tubes and are not as capable of developing the increased pull strength or withstanding the higher fluid pressures attainable with thicker tubes.

Accordingly, it is an object of the present invention to provide a means for attaching an IV tube to a catheter which eliminates gaps and voids between the IV tube and catheter at the point of attachment. It is another object of the present invention to manufacture a multilumen catheter which has structural integrity at the juncture of the IV tubes with the lumens of the catheter to achieve increased pull strength between the IV tubes and the catheter. Yet another object is to provide a means for uniformly attaching a plurality of lumens to the respective lumens of a catheter at the same area of the catheter without the need for stretching or pulling the catheter. It is still another object of this invention to provide an integral attachment between relatively thick IV tubes and catheter lumens having incompatible shapes. Another object is to provide a means for insuring uniform engagement of the outer surface of the IV tube with the lumen sidewall to allow use of a lower and more controllable RF energy level that results in increased tool life and that permits use of thicker walled IV tubes.

SUMMARY OF THE INVENTION

The preferred embodiment of the present invention includes a collet which is made from a dielectric material and dimensioned to clampingly hold a catheter. Also included in the device is a metal adapter which is grounded and which is operatively associated with the dielectric collet for engaging the collet to the catheter. A mandrel which is inserted into an IV tube is positioned within a lumen of the catheter so that the mandrel and a portion of the IV tube can be simultaneously inserted into the catheter lumen. With the mandrel-IV tube combination inserted into the lumen of the catheter, the adapter and associated means are activated to engage the dielectric collet with the catheter to compressingly urge the lumen sidewalls into snug engagement with at least a portion of the outer surface of the IV tube. A generator provides RF energy to the mandrel with sufficient power level to cause a welding and reforming of the IV tube with the side wall of the catheter lumen.

The novel features of this invention, as well as the invention itself, both as to its organization and operation will be best understood from the accompanying drawings, taken in conjunction with the accompanying description, in which similar reference characters refer to similar parts, and in which:

BRIEF DESCRIPTION OF THE DRAWINGS

FIG. 6 is a cross-sectional view of the area of attachment between the IV tube and the catheter;

FIG. 7a is a side view of the dielectric collet along the line 7a—7a of FIG. 8;

FIG. 7b is a side view of the metal collet with portions shown in phantom for illustration and clarification;

FIG. 7c is a side view of the metal adapter of the present invention with portions shown in phantom for illustration and clarification;

FIG. 8 is a top view of the dielectric collet of the present invention; and

FIG. 9 is a top view of the metal collet of the present invention.

DESCRIPTION OF THE PREFERRED EMBODIMENT

Figure 1:
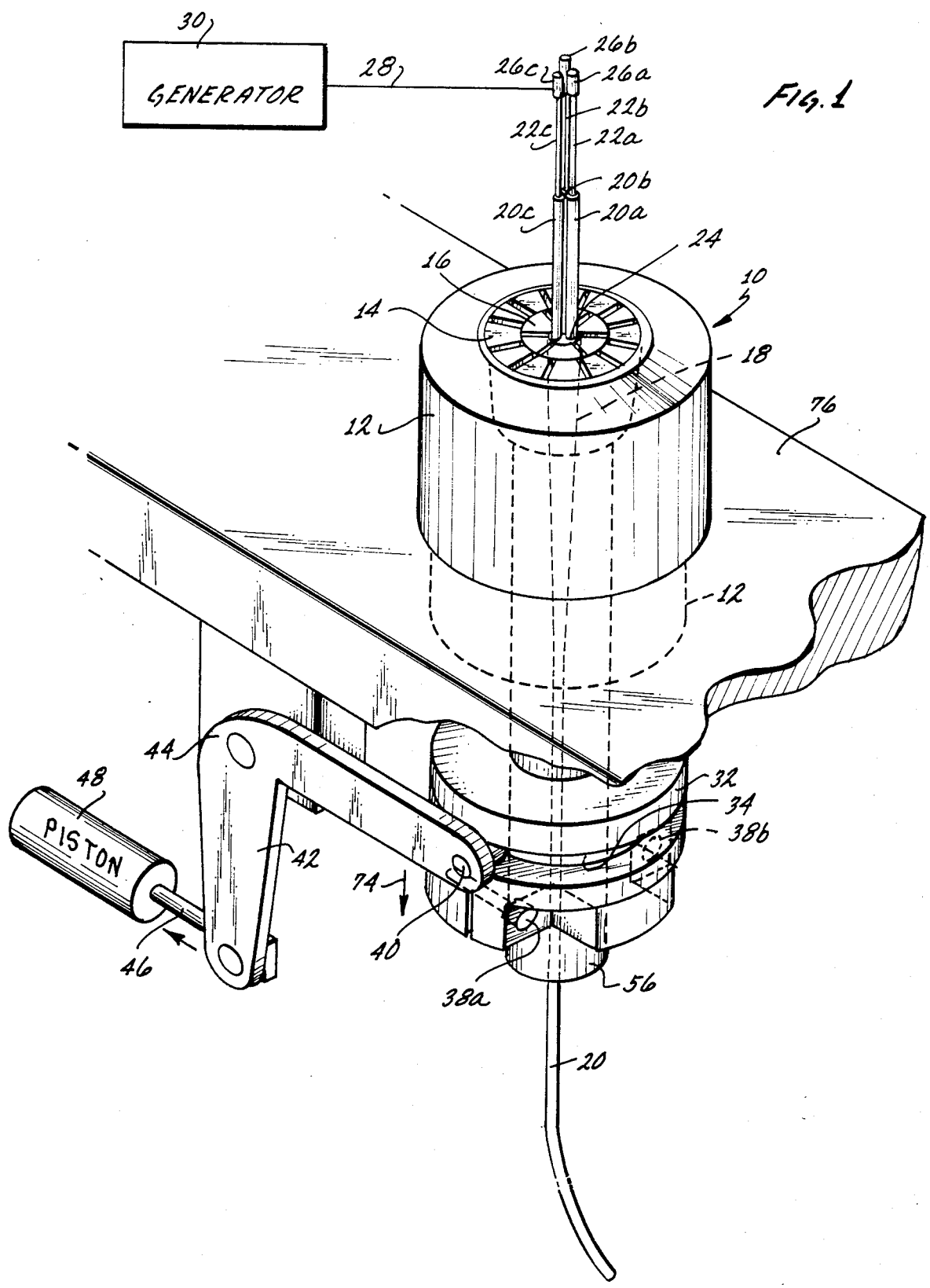
FIG. 1 is a perspective view of the RF welding device having portions broken away and in phantom for illustration and clarification and shown with a mandrel and IV tube in position for the welding operation.
Figure 2:
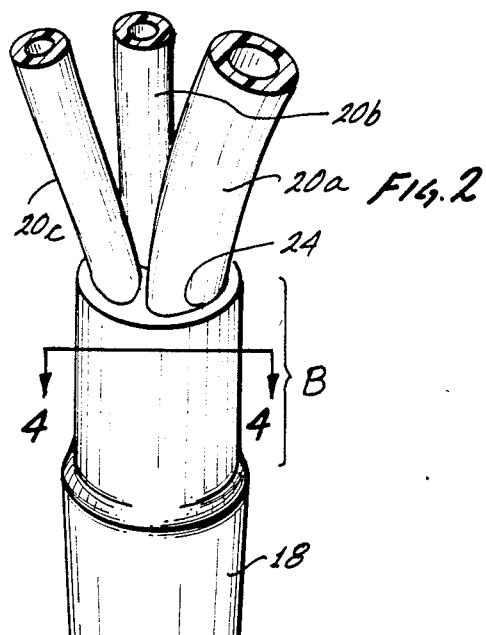
FIG. 2 is a perspective view of the multi-lumen catheter with attached IV tubes.

Referring now to the drawings and particularly to FIG. 1, there is shown a welding device generally indicated by the numeral 10 which incorporates the principals of the present invention. As seen in FIG. 1 a metal adapter 12 is mounted on a support 76. Operatively associated with metal adapter 12 is a metal collet 14 and a dielectric collet 16 which are operatively associated with each other to clampingly engage and hold the catheter 18 within dielectric collet 16. The interrelation of metal adapter 12, metal collet 14 and dielectric collet 16 can best be appreciated by reference to FIGS. 7a, 7b and 7c, which, taken together, show an exploded arrangement of these elements of the present invention. As can be appreciated by cross reference between FIGS. 1, 7a, 7b and 7c, the dielectric collet 16 nests within metal collet 14, and both are operatively associated with the metal adapter 12 in a manner to be subsequently discussed in greater detail.

Still referring to FIG. 1, it is seen that a collar 32 having a peripheral groove 34 is attached to extension 56 of metal collet 14. A semi-circular shaped band 36 is connected with collar 32 by a screw 38a and a second screw 38b which are generally parallel to each other. Screw 38a and 38b are tightened in a manner that grips extension 56 of metal collet 14 between collar 32 and band 36 to prevent relative motion between collar 32 and extension 56. A pivot arm 42 is rotatably mounted on support 76 by a hinge pin 44. Actuator arm 46 is rigidly attached to pivot arm 42 and operatively coupled to piston 48 to rotate pivot arm 42 around hinge pin 44 in accordance with movement of piston 48. A pin 40 is mounted on pivot arm 42 and is slidably received within the slot 34 of collar 32 to raise and lower metal collet 14 along a line generally indicated by directional arrow 74.

Referring now to FIG. 8 and FIG. 7a, it can be seen that dielectric collet 16 comprises a plurality of resilient members 50 which are separated from each other by the slots 52 and which are integrally attached one with each other at the bottom 68 of dielectric collet 16. Each resilient member 50 further comprises an end portion 54 which is dimensioned and adapted to cooperate with the other resilient members 50 of dielectric collet 16 to clampingly engage catheter 18. Dielectric collet 16 is also formed with a pathway 70 so that as the end portions 54 of resilient member 50 grasp a certain part of the catheter 18, the remainder of catheter 18 can extend on through pathway 70. Preferably, dielectric collet 16 is made of a material known in the relevant art as acetal. It should be appreciated, however, that any dielectric material having sufficient strength and resilience to clampingly engage the catheter 18 is sufficient for the purposes of the present invention.

FIG. 9 and FIG. 7b respectively show a top view and a side view of the metal collet 14. As can be perhaps best seen in FIG. 7b, metal collet 14 comprises a plurality of resilient fingers 58 which are separated from each other by the slots 60 and are integrally joined to the extension portion 56 of metal collet 14 in a manner that permits the cooperation of resilient fingers to clampingly engage upon an object. In FIG. 7b it can also be seen that each of the resilient fingers 58 is formed with a flange portion 72 which extends outwardly from resilient fingers 58 and is tapered or flared for a purpose to be subsequently discussed. Formed throughout the longitudinal length of metal collet 14 is a passageway 64 in the region where the resilient fingers 58 are located and a passageway 66 in the region associated with extension 56. Passageway 64 and passageway 66 are dimensioned so that the diameter of the passageway 64 is greater than the diameter of passageway 66. As best seen in FIG. 7b, this change in dimension of passageway 64 creates a base 62 within the metal collet 14. As can be appreciated by reference to FIGS. 1, 7a and 7b, the dielectric collet 16 is dimensioned to nest within the passageway 64 of metal collet 14 with bottom 68 of dielectric collet 16 resting against base 62 of the metal collet 14. In this configuration the top portion of dielectric collet 16 is flush with the top of metal collet 14. It should now be appreciated that a circumferencial force acting upon metal collet 14 will cause resilient fingers 58 to merge and reduce the diameter of passageway 64 in the region where resilient fingers 58 are located. Consequently, metal collet 14 engages resilient members 50 of dielectric collet 16 in a manner that causes resilient members 50 to merge and reduce the diameter of pathway 70 in the area where end portions 54 of dielectric collet 16 are located.

A metal adapter 12, as shown in FIG. 7c is formed with a bore 78 having a tapered region generally designated A in FIG. 7c. Considering FIGS. 7a, b and c together, it can be appreciated that dielectric collet 16 and metal collet 14 are cooperatively positioned as previously discussed and that the combination of dielectric collet 16 and metal collet 14 are dimensioned to be received into the bore 78 of adapter 12. As the metal collet 14 is positioned within bore 78 of adapter 12, it should be appreciated that the tapered portion of the flanges 72 on metal collet 14 engage with tapered region A of the adapter 12. Thus, a movement of the metal collet 14 in the direction indicated by directional arrow 74 in FIG. 7c will increasingly urge tapered region A against flanges 72 to cause a merging of the resilient fingers 58 on metal collet 14. As previously discussed there will be a corresponding merging of the resilient members 50 of dielectric collet 16. It should be further noted that the length of extension of the metal collet 14 is such that it extends through the bore 78 so as to be exposed for operative engagement with the collar 32 as previously discussed and shown in FIG. 1.

In the preferred embodiment of the present invention, adapter 12 and metal collet 14 are made of a beryllium copper alloy. However, adapter 12 may also be made of cold rolled steel and the metal collet 14 may be made of a heat treated spring steel. In either case, or with another material, it is important that metal collet 16 and adapter 12 provide an electrical ground and that metal collet 14 be of sufficient strength and resilience to perform the function of clampingly engaging an object, such as dielectric collet 16, when the object is placed in passageway 64 of the metal collet 14. Further, it can be appreciated by one skilled in the pertinent art that the materials for adapter 12 and metal collet 14 be of sufficient strength to resist continued operation in a manufacturing environment.

Figure 3:
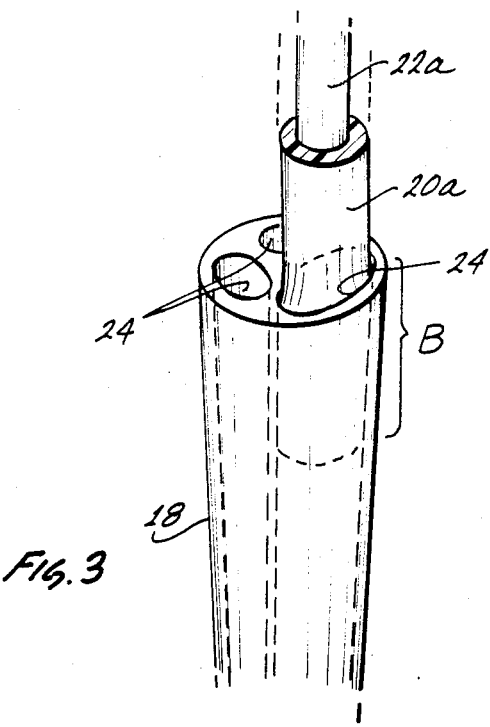
FIG. 3 is a perspective view of the multi-lumen catheter showing an IV tube and mandrel in position for the welding of the IV tube to the catheter.
Figure 4:
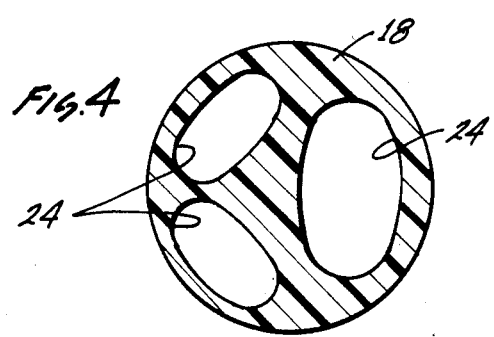
FIG. 4 is a cross-sectional view of the catheter prior to attachment of the IV tubes as seen along the line 4—4 in FIG. 2.
Figure 5:
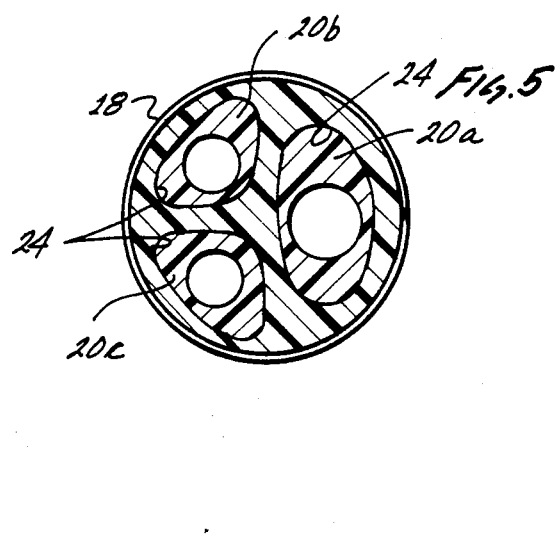
FIG. 5 is a cross-sectional view of the catheter after attachment of the IV tubes as seen along the line 4—4 in FIG. 2.

FIG. 4 shows a typical cross section of a multilumen catheter 18 having eliptical shaped lumens 24 before the catheter 18 is attached in fluid communication with an IV tube 20a. FIG. 3 shows the association of an IV tube 20a with a lumen 24 of catheter 18 during the welding procedure. As can be better seen with reference to FIG. 3 in preparation for the welding procedure, a mandrel 22a is inserted into the passageway of IV tube 20a. The combination of IV tube 20a and mandrel 22a is then inserted into a lumen 24 of catheter 18. Likewise, mandrels 22b and c are respectively inserted into IV tubes 20b and c and separately inserted into lumens 24 of catheter 18. Although only IV tubes 20a, b and c are discussed here, it must be appreciated that more or fewer IV tubes 20 can be used depending only on the number of lumens 24. In the preferred embodiment the mandrels 22a, b and c are made of a beryllium copper alloy. Spring steel, sometimes commonly referred to by those skilled in the art as "piano wire" may, however, also be used for mandrels 22a, b and c. Once the association between IV tubes 20a, b and c and the lumens 24 of catheter 18 has been accomplished, the device 10 can be operated to urge end portions 54 of dielectric collet 16 against catheter 18 to further compressingly engage IV tubes 20a, b and c with lumens 24 of catheter 18. A generator 30 may be of any suitable construction well known in the art which is designed to produce high frequency power for welding plastics and other materials. In the welding operation, generator 30 is connected through a line 28 to connector 26a in a manner well known in the art. The generator 30 is then activated to provide RF energy to the mandrel 22a for welding and reforming the IV tube 20a to the side wall inner surface of a respective lumen 24 in the catheter 18. Sequentially, line 28 can then be connected to mandrels 22b and c and generator 30 activated to weld and reform IV tubes 20b and c with the respective lumens 24.

Although any commonly used material is acceptable, welding device 10 is particularly useful for work with IV tubes 20a, b or c and catheters 18 which are made of polyurethane. A barium-filled polyurethane to provide the radiopacity characteristic of many preferred catheters is acceptable for use with the welding device 10.

It should be appreciated by one skilled in the art that the metal collet 14 can be eliminated from the welding device 10 without affecting the utility or operation of the welding device 10. In an alternate embodiment, the dielectric collet 16 is formed to function like metal collet 14 of the preferred embodiment and made operable in direct association with the adapter 12 to clampingly engage the catheter 18. With this in mind, it should be understood that metal collet 14 is included in the preferred embodiment for the purpose of providing a more rugged device which is capable of withstanding the repetitive operations likely to be encountered in a manufacturing process. The necessity for metal collet 14 is, in part, caused by material limitations. In particular, the acetal material preferably used in the manufacture of dielectric collet 16 is not suited for the repetitive and continuous operation envisioned in the manufacturing process. Dielectric collet 16, however, when nested in passageway 64 of metal collet 14 as intended in the preferred embodiment is not subjected to the stresses and loads which would cause it to wear out early. Regardless, the utility of welding device 10 is dependant upon an electrical connection wherein the IV tube 20a and the catheter 18, in combination with a dielectric, separate mandrel 22 from an electrical ground. According to the present invention, metal collet 14 and adapter 12 provide the ground. As easily understood by those skilled in the pertinent art, any ground will do. Thus metal adapter 12 alone, as described for an alternate embodiment, will suffice and metal collet 14 could, in fact, be eliminated.

To more fully understand and appreciate the structure of catheter 18 and the attachment of IV tubes 20a, b and c thereto, collective reference is made to FIGS. 2, 3, 4, 5 and 6. FIG. 4 shows a typical cross section of catheter 18 having eliptical shaped lumens 24. On the other hand, IV tubes 20a, b and c typically have generally circular cross-sections. Thus, IV tubes 20a, b and c are incompatible for a directly conforming fit with the eliptical cross-section of lumens 24. Nevertheless, the compressive action of dielectric collet 16 and the subsequent reforming and welding operation mentioned above create a bonded conformity between the outside surfaces of IV tubes 20a, b and c and the respective lumens 24. As seen in the cross-section of catheter 18 in FIG. 5, the result is a continuous and integral bond between the IV tubes 20a, b and c and the lumens 24 of catheter 18. Furthermore, this bond is continuous throughout the region B indicated in FIGS. 2 and 3. In the final configuration, the catheter 18 and the attached IV tubes 20a, b and c provide a device of unitary construction which is a structural continuum at the juncture of tube 20 and lumen 24.

Also, due to the compressive action of device 10 on catheter 18 during the welding operation, it is possible to use IV tubes 20a, b and c having thicker walls than would otherwise be possible. Indeed, in the preferred embodiment, wall thicknesses from 0.020 inches to 0.030 inches are not uncommon. Of course, walls thinner than 0.020 inches are also suitable for the present invention and walls thicker than 0.030 inches may be used depending on the compressive strength of the device 10 and the amount of RF power supplied by generator 30.

As shown in FIG. 6, in the preferred embodiment for catheter 18, IV tube 20 is formed with a chamfered tip 80 at the end of IV tube 20 that is inserted into and welded to catheter 18. The chamfered tip 80, so positioned, permits entry of a guidewire (not shown) between lumen 24 and IV tube 20 without hanging up the guidewire (not shown) at the juncture of the end of IV tube 20a with the lumen 24. The chamfered tip 80 also helps prevent air bubble immobilization and fluid stagnation areas at the juncture. In order to further facilitate passage of the guidewire (not shown) from lumen 24 into an IV tube 20, each lumen 24 may be preformed to establish a step 82 within the lumen 24 against which the chamfered tip 80 of IV tube 20 can be positioned. As best seen in FIG. 6, the step 82 permits an unobstructed transition for passage of the guidewire (not shown) from lumen 24 onto the chamfered surface of chamfered tip 80 and into IV tube 20. Step 82 can be preformed by inserting into a lumen 24 a mandrel (not shown) having a cross-sectional area that is substantially equivalent to the cross-sectional area of lumen 24. Sufficient RF energy from generator 30 is then supplied to the mandrel to reform lumen 24 and shape step 82.

Not shown in the drawings are the plethora of adapters and connectors which can be attached to the proximal ends of IV tubes 20a, b and c opposite from the end of their attachment with the catheter 18. As can be appreciated by those skilled in the art, such connectors can be preattached or attached as needed and can have a variety of structures dependent only on the needs of the operator. Generally, however, it is anticipated that a standard luer adapter will be most commonly incorporated.

As previously mentioned, a suitable material for the catheter 18 is a barium-filled polyurethane. In the contemplation of the present invention, IV tubes 20a, b and c are also made of a polyurethane material. The use of the same material throughout the catheter 18 and IV tube 20 combination obviates any differences in strength, durability or compatability which may occur when dissimilar materials are used. Although the expressed preference for the present invention is the use of a polyurethane material, other materials which are well known in the art and suitable for an RF welding operation may be used. In fact, dependent only on the desires of the manufacturer, the catheter 18 and IV tubes 20 may even be of dissimilar materials.

OPERATION

In the operation of the welding device 10, a mandrel 22a having electrical conductive properties, such as beryllium copper alloy, is inserted into the passageway of an IV tube 20a. The mandrel 22a and IV tube 20a combination is then inserted into a lumen 24 of a catheter 18. Likewise, mandrels 22b and c are respectively inserted into IV tubes 20b and c and these combinations are positioned into lumens 24 of catheter 18. As previously discussed the proper operation of welding device 10 is not dependent on cross-sectional conformity between the IV tube 20a, b and c and the lumens 24.

Once the combination of IV tubes 20a, b and c and mandrels 22a, b and c are inserted into lumens 24 of catheter 18, the entire combination of mandrel 22a, b and c, IV tube 20a, b and c and catheter 18 is positioned within the pathway 70 of dielectric collet 16 as shown in FIG. 1. Piston 48 is then activated to move metal collet 14 in the direction indicated by directional arrow 74 in FIG. 1. This motion causes the flanges 72 of metal collet 14 to urge against the tapered region A of adapter 12 and clampingly engage the resilient fingers 58 of metal collet 14 onto the dielectric collet 16. The urging of metal collet 14 onto dielectric collet 16 in turn causes resilient members 50 of dielectric collet 16 to clampingly engage with the catheter 18.

It should be appreciated from previous discussions that the compressive forces generated by the action of dielectric collet 16 on the catheter 18 causes the reshaping of lumens 24 and IV tubes 20 in a manner to cause a uniform and continuous contact between the outside surface of the IV tubes 20 and the side walls of lumens 24. Thus, as can be appreciated from the previous discussion, a generally circular cross-section IV tube 20 can be made to come in contact with a substantially eliptically shaped lumen 24. It should be further appreciated that the lumen 24 need not be restricted to a substantially eliptical shape. Indeed, other shapes such as semi-circles, squares or rectangles could also be used. An important feature of the present invention, as illustrated by the welding device 10 in FIG. 1, is that the compression caused by the dielectric collet 16 on the catheter 18 overcomes dimensional inconsistencies and particularly this compression overcomes dimensional inconsistencies of soft extruded materials, such as polyurethane, which are typically used in IV tubes and catheters.

With the catheter 18, IV tubes 20 and mandrels 22 positioned within the welding device 10 as shown in FIG. 1 and after welding device 10 has been operated to compress the dielectric collet 16 onto catheter 18, the exposed end of mandrel 22a opposite from the end which is associated with catheter 18 is electrically connected to a connector 26a. Connector 26a, which is in electrical contact with generator 30 through line 28, provides means for supplying RF energy from generator 30 to mandrel 22a. As previously discussed, by overcoming the dimensional inconsistencies through compression of the catheter 18 onto IV tube 20, contact between the side wall of lumen 24 and the outer surface of IV tube 20 is assured. Thus, the initial compatability or incompatability of configuration between the IV tube and the shape of lumen 24 becomes less important. A beneficial effect of this fact is that thicker walled IV tubes 20 can be welded into lumen 24 with less power required from generator 30. It is not uncommon to consider operation of the welding device 10 within a range of power supplied to mandrel 22 of from 300 to 1,000 watts.

Once the mandrels 22a, b and c, IV tubes 20a, b and c and catheter 18 combination have been placed in the welding device 10, the power supply 30 is energized and energy is passed along mandrel 22a to weld IV tube 20a to catheter 18. Sequentially, energy from generator 30 is applied to mandrels 22b and c to weld IV tubes 20b and c to catheter 18. After the welding operation is completed, the catheter 18 and IV tubes 20a, b and c are allowed to cool for a period of time. The welding device 10 is then operated to move the metal collet 14 in a direction opposite to directional arrow 74. This releases the grip or clamping effect of dielectric collet 16 on catheter 18. The catheter 18 and IV tube 20a combination can then be removed from welding device 10 and mandrels 22a, b and c can be removed from IV tubes 20a, b and c.

Catheter 18 can be dimensioned for adaptability and use as a venous catheter. When so used, the unitary construction for catheter 18, as described above, provides for multiple fluid passageways defined by the individual proximal IV tubes 20 and their associated lumens 24. As previously stated, the end of each individual IV tube 20 opposite from the catheter 18 can be specially adapted for connection with a particular fluid source (not shown). As can be appreciated by those skilled in the relevant art, the various fluid sources suitable for use with catheter 18 include IV pumps, IV controllers, IV bottles, syringes, and other specialized fluid containers. Regardless of the particular fluid source used, catheter 18 when properly positioned into the vein of a patient and the IV tubes 20 associated with catheter 18 provide an effective means for infusing medical solutions to the patient.

While the particular RF welding device as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. A device for RF welding an IV tube to a multilumen catheter comprising:
    means cooperative with said catheter for compressively engaging a portion of said IV tube with a dimensionally incompatible portion of a lumen of said catheter;
    an electrically conductive mandrel insertable into said IV tube;
    an electrical ground associated with said compressive means; and
    means connectable with said mandrel for generating RF energy between said mandrel and said ground to weld a continuous and integral bond at the interface between said IV tube and said catheter.

2. A device for RF welding an IV tube to a multilumen catheter as recited in claim 1 wherein said compressive means further comprises a collet.

3. A device for RF welding an IV tube to a multilumen catheter as recited in claim 2 wherein said collet is made of a dielectric material.

4. A device for RF welding an IV tube to a multilumen catheter as recited in claim 3 wherein said mandrel is made of beryllium copper alloy.

5. A device for RF welding an IV tube to a multilumen catheter as recited in claim 4 further comprising:
    a metal collet operatively associated with said dielectric collet for urging said dielectric collet into compressive engagement with said catheter; and
    means to activate said metal collet.

6. A device for RF welding an IV tube to a multilumen catheter as recited in claim 5 wherein said metal collet is made of beryllium copper alloy.

7. A device for RF welding an IV tube to a multilumen catheter as recited in claim 6 further comprising:
    an adapter having a bore to slidably receive said metal collet for operative association therewith to activate said metal collet; and
    means for reciprocally sliding said metal collet within the bore of said adapter.

8. A device for RF welding an IV tube to a multilumen catheter as recited in claim 7 wherein said catheter and said IV tubes are made of polyurethane.

9. A device for RF welding an IV tube to a multilumen catheter as recited in claim 8 wherein said catheter is made of a radiopaque polyurethane.

10. A device for welding an IV tube in fluid communicating with a lumen of a catheter comprising:
    a support;
    a grounded adapter having a tapered bore therethrough mounted on said support;
    a metal collect forming a passageway and slidably disposed in the tapered bore of said adapter for operative association therewith;
    a dielectric collect disposed in the passageway of said metal collet and operatively associated with said metal collet for clamping engagement with said catheter;
    a metal mandrel insertably engaged with said IV tube;
    means for clamping said dielectric collet onto said catheter;

means for positioning at least a portion of said IV tube-mandrel combination into said lumen; and means for applying RF energy to said mandrel for welding said IV tube to said lumen.

11. A welding device as recited in claim 10 wherein said adapter, said metla collet and said mandrel are made of a beryllium copper alloy.

12. A welding device as recited in claim 11 wherein said IV tube and said catheter are made of polyurethane.

13. A welding device as recited in claim 12 wherein said catheter is made of a radiopaque polyurethane.

14. A method for RF welding an IV tube into fluid communication with a lumen of a catheter comprising the steps of:

a. positioning at least a portion of said IV tube into a portion of the lumen of said catheter;

b. placing said IV tube and catheter combination in operative association with a device comprising a support, a grounded adapter having a tapered bore therethrough mounted on said support, a metal collet forming a passageway and slidably disposed in the tapered bore of said adapter for operative association therewith, a dielectric collet disposed in the passageway of said metal collet and operatively associated with said metal collect for clamping engagement with said catheter, a metal mandrel insertably engaged with said IV tube, and means for clamping said dielectric collet onto said catheter;

c. activating said device to clampingly engage said dielectric collet with said catheter; and d. applying RF energy to said mandrel for welding said IV tube to said lumen.

15. A device for RF welding an IV tube to a multilumen catheter comprising:

a dielectric collet cooperative with said catheter for compressively engaging a portion of said IV tube with a portion of a lumen of said catheter;

an electrically conductive mandrel insertable into said IV tube;

a metal collet for providing an electrical ground and operatively associated with said dielectric collet for urging said dielectric collet into compressive engagement with said catheter;

an adapter having a bore to slidably receive said metal collet for operative association therewith to activate said metal collet;

means for reciprocally sliding said metal collet within the bore of said adapter; and means connectable with said mandrel for generating RF energy between said mandrel and said metal collet to weld a continuous and integral bond at the interface between said IV tube and said catheter.

16. A device as recited in claim 15 wherein said mandrel and said metal collet are made of beryllium copper alloy.

17. A device as recited in claim 16 wherein said catheter and said IV tubes are made of polyurethane.

18. A device a recited in claim 17 wherein said catheter is made of a radiopaque polyurethane.

* * * * *